(12) United States Patent (10) Patent No.: US 12,605,175 B2

Dunn (45) Date of Patent: Apr. 21, 2026

(54) CONTOURED SURGICAL FORCEPS

(71) Applicant: University of Massachusetts, Boston, MA (US)

(72) Inventor: Raymond Dunn, Shrewsbury, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 16/254,290

(22) Filed: Jan. 22, 2019

(65) Prior Publication Data

US 2019/0282256 A1 Sep. 19, 2019

Related U.S. Application Data

(63) Continuation of application No. 14/696,305, filed on Apr. 24, 2015, now Pat. No. 10,201,362.

(60) Provisional application No. 61/983,994, filed on Apr. 24, 2014.

(51) Int. Cl.
  *A61B 17/30* (2006.01)
  *A61B 17/00* (2006.01)

(52) U.S. Cl.
  CPC .... *A61B 17/30* (2013.01); *A61B 2017/00424* (2013.01); *A61B 2017/00429* (2013.01); *A61B 2017/0046* (2013.01)

(58) Field of Classification Search
  CPC .......... A61B 17/30; A61B 2017/00424; A61B 2017/00429; A61B 2017/0046; A61B 2017/0042; A61B 2017/00433; A61B 2017/305; A46B 5/026; B25G 1/102; B25G 1/105
  See application file for complete search history.

(56) References Cited

U.S. PATENT DOCUMENTS

| | | | |
|---|---|---|---|
| 3,167,981 | A | 2/1965 | Kern |
| 3,592,247 | A * | 7/1971 | Solf ...................... B25G 1/105 |
| | | | 81/177.1 |
| 4,634,165 | A | 1/1987 | Russell et al. |
| 4,753,235 | A | 6/1988 | Hasson |
| 4,938,214 | A | 7/1990 | Specht et al. |
| 4,955,887 | A | 9/1990 | Zirm |
| 5,089,007 | A * | 2/1992 | Kirsch ................... A61B 17/32 |
| | | | 606/205 |
| 5,254,131 | A | 10/1993 | Razi |
| 5,290,302 | A | 3/1994 | Pericic |
| D355,455 | S | 2/1995 | Stolte |
| 5,501,698 | A | 3/1996 | Roth et al. |
| 5,578,050 | A | 11/1996 | Webb |
| 5,634,918 | A | 6/1997 | Richards |

(Continued)

OTHER PUBLICATIONS

U.S. Appl. No. 29/488,962, filed Apr. 24, 2014, U.S. Pat. No. D. 762,302.

(Continued)

*Primary Examiner* — Diane D Yabut

(74) *Attorney, Agent, or Firm* — McCarter & English, LLP

(57) ABSTRACT

A contoured forceps handle is presented having a first arm with a contoured surface and a second arm with a contoured surface to provide for rotation in the hand of a user. The forceps handle may be used with a forceps or may have tips attached. Contoured forceps onlays are also presented that may be attached to forceps.

26 Claims, 10 Drawing Sheets

(56)                  References Cited

U.S. PATENT DOCUMENTS

| | | | | |
|---|---|---|---|---|
| 6,051,011 | A * | 4/2000 | Weidenbenner | A61F 9/00763 |
| | | | | 606/174 |
| 6,364,891 | B1 | 4/2002 | Doble | |
| 6,533,797 | B1 | 3/2003 | Stone et al. | |
| 6,855,156 | B2 | 2/2005 | Etter et al. | |
| D504,176 | S | 4/2005 | Vijfvinkel | |
| 7,208,004 | B2 | 4/2007 | Murdoch | |
| 8,585,735 | B2 | 11/2013 | Nallakrishnan | |
| 8,657,851 | B2 | 2/2014 | Aufaure et al. | |
| 8,974,480 | B2 | 3/2015 | Terao | |
| D762,302 | S | 7/2016 | Dunn | |
| D797,284 | S | 9/2017 | Dunn | |
| 10,201,362 | B2 | 2/2019 | Dunn | |
| 2002/0016591 | A1 | 2/2002 | Levine et al. | |
| 2003/0014842 | A1 * | 1/2003 | Niendorf | A61C 17/08 |
| | | | | 16/430 |
| 2006/0031994 | A1 | 2/2006 | Willat et al. | |
| 2006/0207043 | A1 * | 9/2006 | Yamamoto | A46B 5/026 |
| | | | | 15/167.1 |

| | | | |
|---|---|---|---|
| 2009/0030448 | A1 | 1/2009 | Andre |
| 2010/0004677 | A1 | 1/2010 | Brostoff et al. |
| 2010/0011541 | A1 | 1/2010 | Tillim |
| 2010/0324577 | A1 | 12/2010 | Dunn |
| 2012/0041457 | A1 | 2/2012 | De Vries et al. |
| 2012/0116361 | A1 | 5/2012 | Hanlon et al. |
| 2012/0116370 | A1 | 5/2012 | Tschida |
| 2013/0085326 | A1 | 4/2013 | Scheller et al. |
| 2014/0052116 | A1 | 2/2014 | Herzon |
| 2014/0088639 | A1 | 3/2014 | Bartels et al. |
| 2014/0121697 | A1 | 5/2014 | Scheller et al. |
| 2014/0142603 | A1 | 5/2014 | Scheller et al. |

OTHER PUBLICATIONS

U.S. Appl. No. 14/696,305, filed Apr. 24, 2015, U.S. Pat. No. 10,201,362.

U.S. Appl. No. 29/567,509, filed Jun. 9, 2016.

U.S. Appl. No. 29/589,246, filed Dec. 29, 2016, U.S. Pat. No. D. 797,284.

* cited by examiner

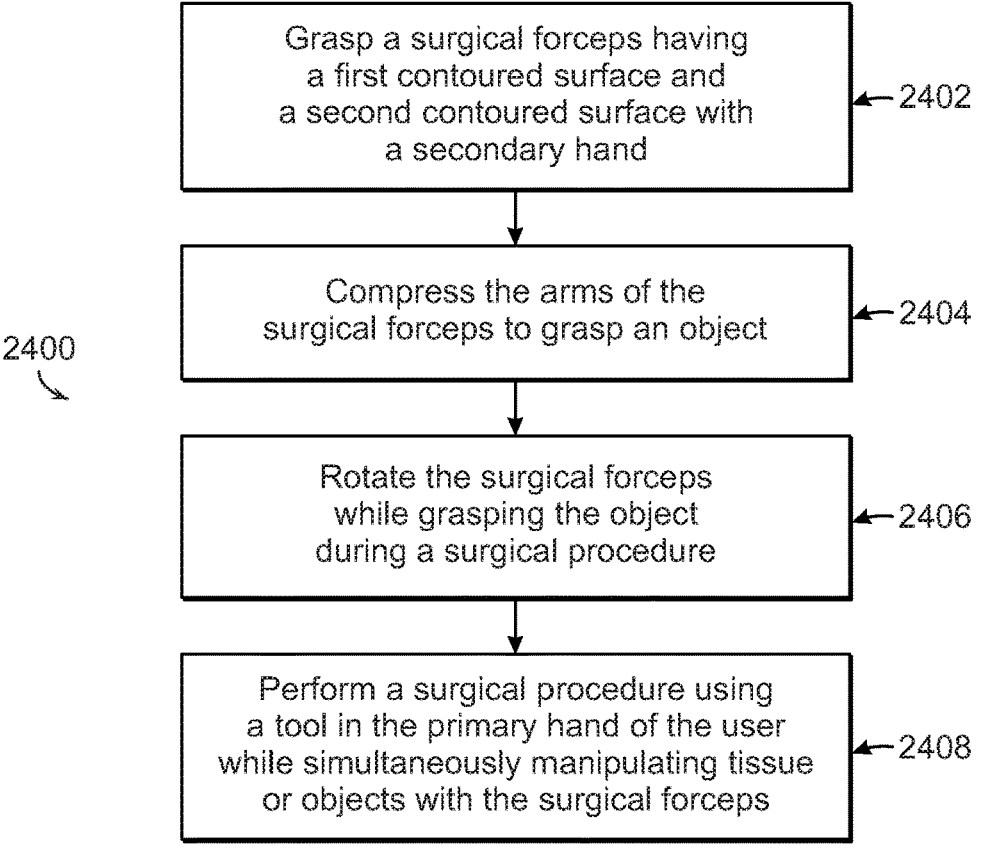

Grasp a surgical forceps having
a first contoured surface and
a second contoured surface with
a secondary hand ←—2402

Compress the arms of the
surgical forceps to grasp an object ←—2404

Rotate the surgical forceps
while grasping the object
during a surgical procedure ←—2406

Perform a surgical procedure using
a tool in the primary hand of the user
while simultaneously manipulating tissue
or objects with the surgical forceps ←—2408

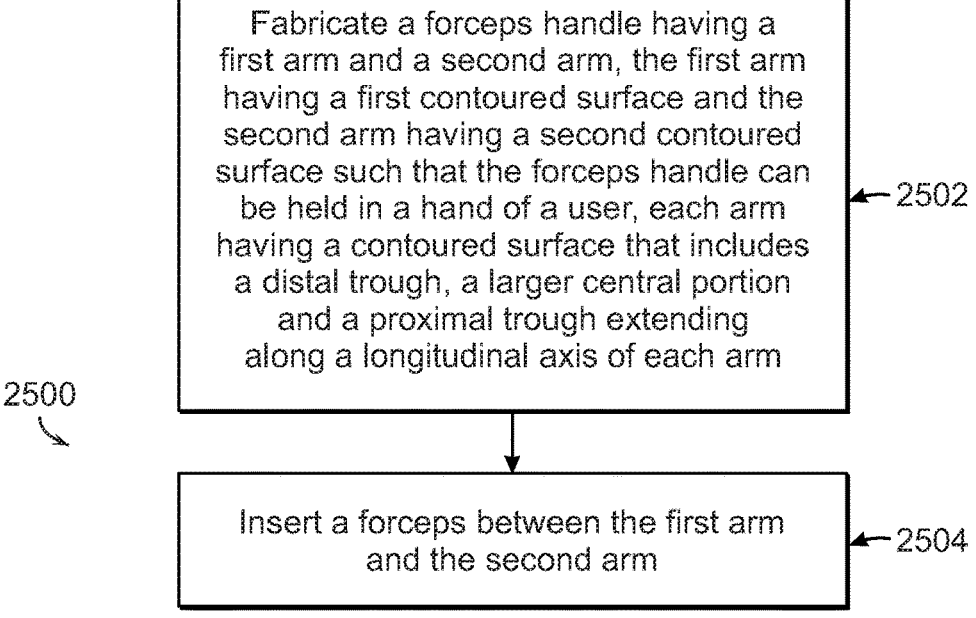

Fabricate a forceps handle having a
first arm and a second arm, the first arm
having a first contoured surface and the
second arm having a second contoured
surface such that the forceps handle can
be held in a hand of a user, each arm
having a contoured surface that includes
a distal trough, a larger central portion
and a proximal trough extending
along a longitudinal axis of each arm ←—2502

Insert a forceps between the first arm
and the second arm ←—2504

CONTOURED SURGICAL FORCEPS

RELATED APPLICATIONS

This application is a continuation of U.S. patent application Ser. No. 14/696,305, filed Apr. 24, 2015, which claims benefit of U.S. Provisional Patent Application No. 61/983,994, filed on Apr. 24, 2014, the entire contents of the above applications being incorporated herein by reference.

BACKGROUND OF THE INVENTION

Surgical forceps have been in wide use to provide for grasping and precise manipulation of objects or tissue in proximity to surgical sites. Surgeons frequently use forceps to hold and manipulate tissue with their secondary hand, that is, their primary hand is used to perform a procedure such as cutting or suturing while their secondary hand uses the forceps to manipulate the tissue at the same time. This process can be prolonged, frequently lasting many hours, resulting in fatigue. Frequently wounds or incisions require movement within confined spaces and the combination of fatigue and the need for precision can adversely impact surgical outcomes. Frequently, the surgeon must rotate his entire arm at the shoulder, as the flat forceps handle that is frequently used in operating rooms cannot be rotated easily without risk of damaging tissue. There is also a need for sterility and cost effective solutions in medical care so that surgical instruments can be repeatedly used and sterilized without loss of performance. Thus, an ongoing need exists for improvements in surgical implements to both lower cost and improve the quality of care.

SUMMARY OF THE INVENTION

The present invention relates to forceps having a geometry suitable for precise grasping and manipulation required in many surgical procedures. A preferred embodiment of the invention uses contoured arms having generally rounded surfaces along their longitudinal length. This shape enables the surgeon to easily rotate the forceps to different angles to reduce the need to hold the handle differently. This enables rotation of the forceps within a body cavity without a substantial change of arm position and viewing angle. The contoured surface provides an increase in the grasped surface area thereby increasing the amount of functional contact at many angles.

A preferred embodiment provides an integral molded body that includes arms connected by a hinge mechanism, or flexible arms that provide for rotation about a hinge point or one or more axes of rotation. The user can apply pressure with their fingers to compress the arms, and the attached tips of the forceps, towards each other. The user can release pressure such that the spring force of the arms causes the arms to separate. The amount of resilience can be selected during manufacture depending upon the application.

This present invention further relates to a forceps adapter that can be attached to a forceps. The arm adapter provides rounded arm elements that are easier to hold, thereby giving the surgeon greater control and ability to more precisely manipulate objects or tissues. The adapter of the present invention includes a cavity extending between the arms that receives the proximal end of the forceps such that the tips extend from the distal end of the adapter. An outer surface region of the adapter includes handle elements that are gripped manually by the hand of the user during a surgical procedure. The handle elements have contoured surfaces to provide for proper orientation of the tips of the forceps relative to the surgical site. The contoured surface of the handle elements can include a proximal section with a thicker diameter that tapers to a smaller diameter section at the distal end. The distal section can have a recess for the thumb of the user. The tips can be rigidly oriented relative to the surface features to improve manual manipulation. The handle elements can be shaped for left or right handed use.

In accordance with a preferred embodiment, the method for using the adapter of the present invention involves selecting a forceps, inserting it into the adapter, performing the selected procedure, removing the forceps for cleaning, sterilization, and reuse, and either sterilizing or disposing of the adapter.

In another preferred embodiment, the handle elements are an onlay that is assembled with the forceps during manufacture. The elements in this embodiment can be made of a material suitable for sterilization after use. The elements can be molded as unitary bodies with selected portions of the surface having a hatched, braided, or dimpled surface to provide frictional surface regions unlikely to slip when grasped by the user.

The forceps handle can be manufactured using an injection molding or 3D printing process. A molded plastic material may be used and can be adapted for single use (disposable), or alternatively, manufactured using a material suitable for sterilization procedures for reuse. The forceps handle elements can be color coded such that the color can indicate a particular size and/or type of forceps for the type of procedure.

Many applications require the forceps to have a spring force that is preferably within a range that aids the surgeon in the sensation of force feedback during tissue manipulation. It is preferred in certain embodiments to apply limited forces of compression, as well as limited torque during rotation of the forceps, to avoid damaging the tissue. It is further desirable to have a sufficient spring force operating to separate the arms of the forceps to release the tissue in a predictable way. The two arms of the forceps preferably are not displaced laterally during rotation thereof while grasping tissue, that is, the arms must have sufficient lateral rigidity that they remain aligned with the application of torques directed in opposite rotational directions on each arm.

The surgical forceps enable the grasping of different sizes of objects or tissue features. The increase in surface area on the contoured grasping surfaces, and the resulting increase in tactile feedback, improves the range of force that can be applied.

DESCRIPTION OF THE DRAWINGS

FIG. 24 illustrates a method of use of a surgical forceps in accordance with various embodiments of the present invention.

FIG. 25 illustrates a method of assembly of a surgical forceps in accordance with various embodiments of the present invention.

DETAILED DESCRIPTION OF THE INVENTION

Figure 1:
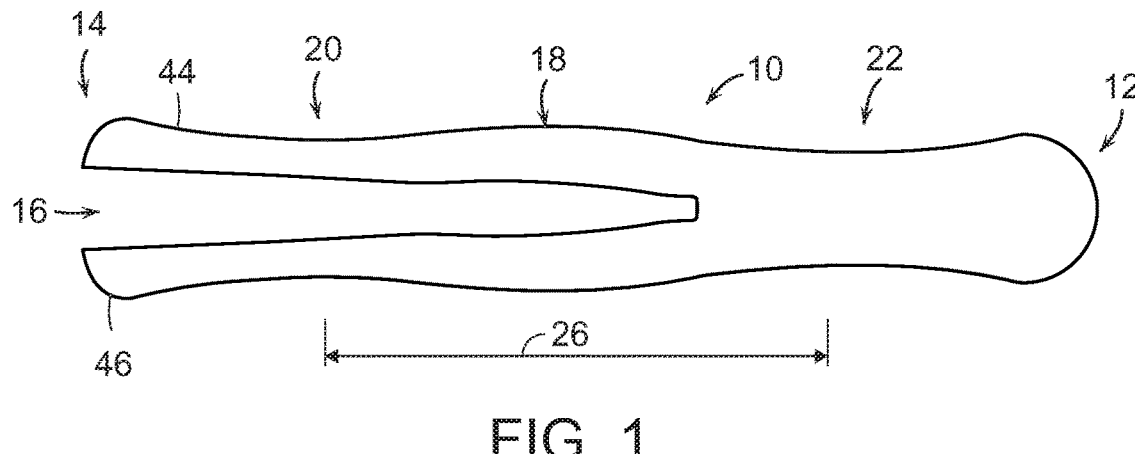
FIG. 1 is a side view of a contoured forceps sleeve in accordance with a preferred embodiment of the present invention.

The foregoing and other features and advantages of the systems and methods for using contoured forceps will be apparent from the following more particular description of preferred embodiments of the system and method as illustrated in the accompanying drawings in which like reference characters refer to the same parts throughout the different views.

A preferred embodiment of the invention relates to a forceps adapter that can be attached to existing forceps. The adapter can be elliptical in shape at least along a longitudinal portion thereof and crosshatched or beveled to give the handle a more natural feel thereby making it easier to hold to provide superior manipulation.

The adapter can be a sterilizable or disposable, contoured plastic handle that can be used on existing forceps. In addition to making the handle of the forceps easier to hold, the design of the adapter also has the advantage of making the handle less slippery than the traditional steel handle. Through use of the adapter, the forceps are easier to manipulate thereby allowing the precision of the grasping and manipulation to be increased and to reduce user fatigue over the course of use.

FIGS. 1 through 4 illustrate a preferred embodiment of the invention where a forceps adapter 10 can be attached to a forceps. FIG. 1 is a side view of the adapter which is divided into a proximal portion 12, a distal portion 14, and a central portion 18. The proximal portion 12 has a generally circular or elliptical cross-sectional shape. A cavity 16, which separates a first arm 44 from a second arm 46, extends through the distal portion 14 and into the central portion 18. The cavity 16 is adapted to accept forceps 40 (as shown in FIG. 4).

Between the distal and central portions is a first concave section 20 or trough adapted to be grasped by the thumb/forefinger and middle finger of the user. Between the central portion and the proximal portion is a second concave section 22 or trough adapted to rest in the web of the user's hand between the thumb and forefinger.

The dimensions of the handle portion are selected to provide for precision and control of the blade during use as well as comfort to the user. The dimensions of the handle features are also of importance as they maximize contact surface area to improve tactile feeling of the handle in the user's hand, which increases the user's sensitivity to the amount of gripping force being applied to the forceps. A common grip of the forceps is the pencil grip where the thumb, forefinger, and middle finger of the user's hand provide three points of contact in the first trough section 20. In a preferred embodiment, the first trough 20 of each arm has a partially circular cross-section with a lateral diameter or width in the range of 1.0-1.5 cm, preferably about 1.2-1.4 cm. In a distal direction from the trough 20, the diameter of the handle increases to prevent the fingers from sliding distally toward the tips of the forceps extending distally from the adapter, particularly when more force is exerted in a distal direction. The larger diameter distal portion 14 has a flared diameter in the range of 1.2 to 1.8 cm, preferably about 1.4-1.6 cm. The central portion 18 has a diameter in the range of 1.6 to 2.0 cm, preferably about 1.8 cm. The larger central portion increases the area of contact with the fingers to further stabilize the device in the user's hand. The second trough 22 has a diameter in the range of 1.0 to 1.5 cm, preferably about 1.2-1.4 cm. The second trough fits within the web extending between the user's thumb and forefinger. The proximal portion 12 is flared, with a diameter in the range of 1.4 to 2.0 cm, preferably 1.6-1.8 cm.

Figure 2:
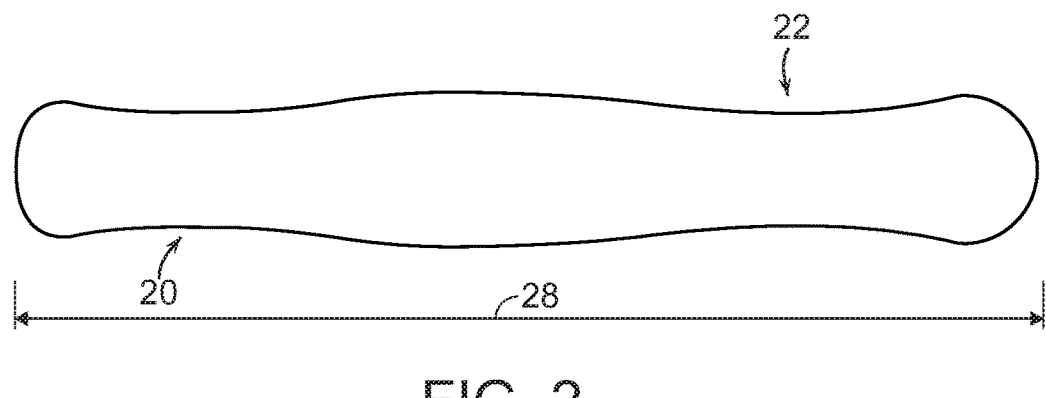
FIG. 2 is a view from the top or bottom of a contoured forceps sleeve in accordance with a preferred embodiment of the present invention.

These dimensions are correlated with the longitudinal distance between features to achieve the described fit to the user's hands. The distance 26 between the minimum trough diameters is a range of 5-7 cm, preferably about 6 cm. The distance 28 from the distal end of the adapter to the proximal end of the adapter as seen in FIG. 2 is in a range of 6-20 cm, depending on the application.

Figure 3:
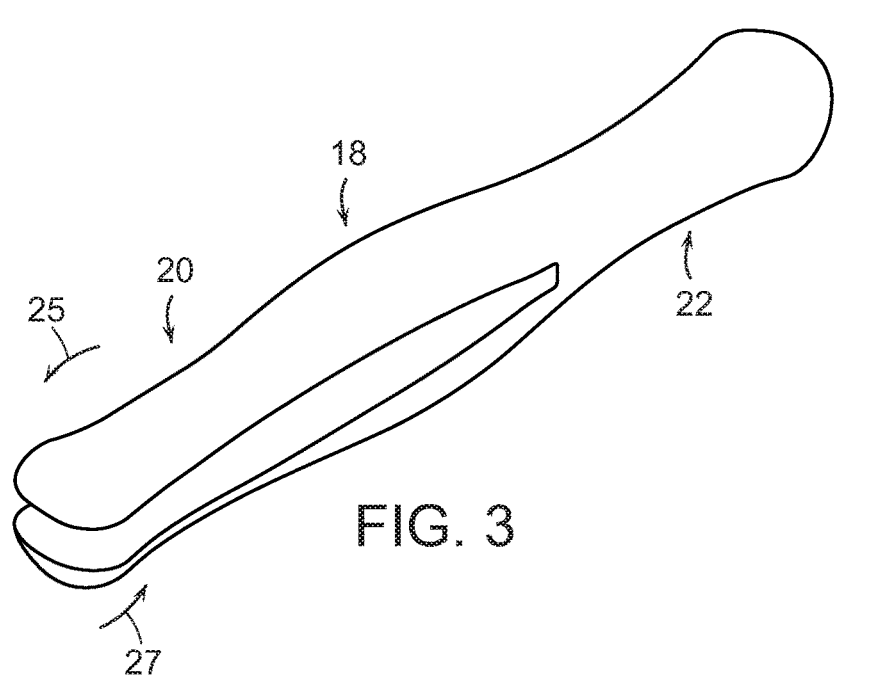
FIG. 3 is a front side perspective of a contoured forceps sleeve in accordance with a preferred embodiment of the present invention.

An important factor in surgical applications is the need to rotate the forceps, frequently with the secondary or second hand of the surgeon. As seen in FIG. 3, as one arm rotates 25 through a 20-60 degree angle, the second arm generally rotates 27 through the same angle but can experience an oppositely directed force imparted by the grasped object to both arms which may be connected to the body of the patient. The grasping of a ligament, an artery, or a bone can result in such forces being imparted to the forceps.

Precise control of the forceps during use is critical. If the handle is awkward to hold, this can contribute to fatigue and the difficulty of the procedure by compelling the user to awkwardly grasp the tool to achieve the proper angle and level of force required to grasp and manipulate the object or tissue as needed. Thus, proper balance, good contact between the user's hand and the handle, and the ability to rotate the handle without having to grip the tool differently can be of great importance. Further, in contrast to traditional flat sided forceps, which can only be rotated approximately 60 degrees without moving hand position, the rounded contours of the adapter 10 allow for the forceps to be comfortably rotated up to 90 degrees.

Figures 4A, 4B:
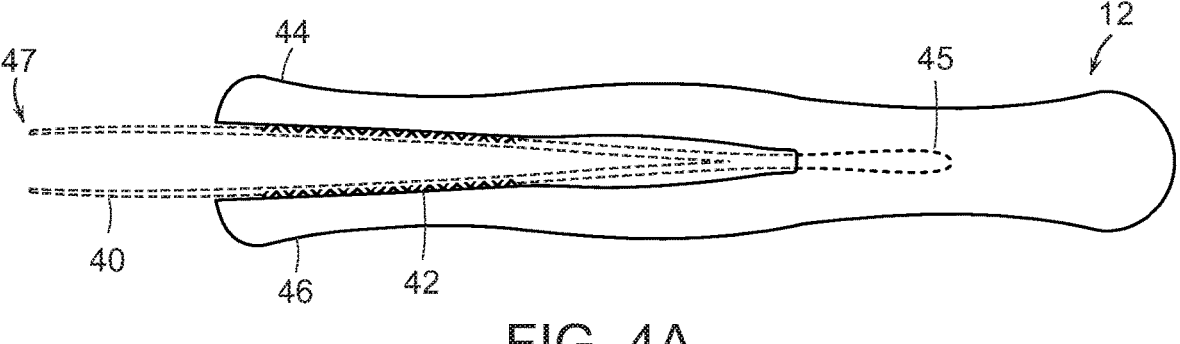
FIGS. 4A-4B are side views of a contoured forceps sleeve and forceps in the open and closed positions, respectively, in accordance with a preferred embodiment of the present invention.
Figure 5:
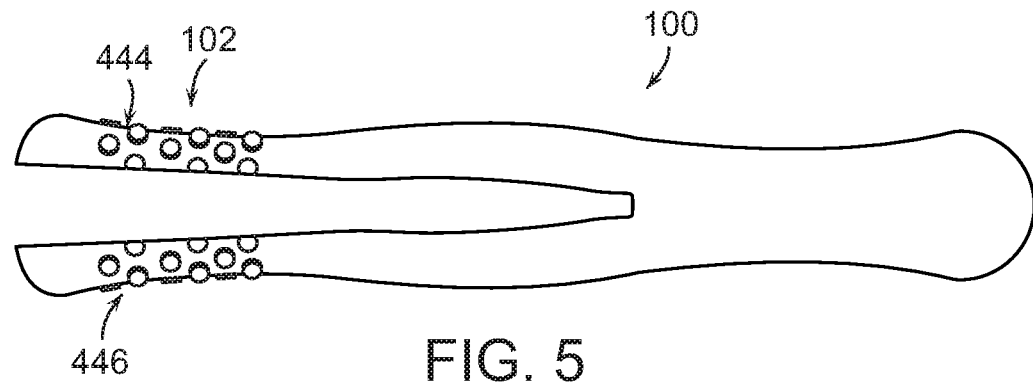
FIG. 5 is a side view of a contoured forceps sleeve having a textured region to enhance grasping by the thumb and forefinger of the user in accordance with a preferred embodiment of the present invention.
Figure 6:
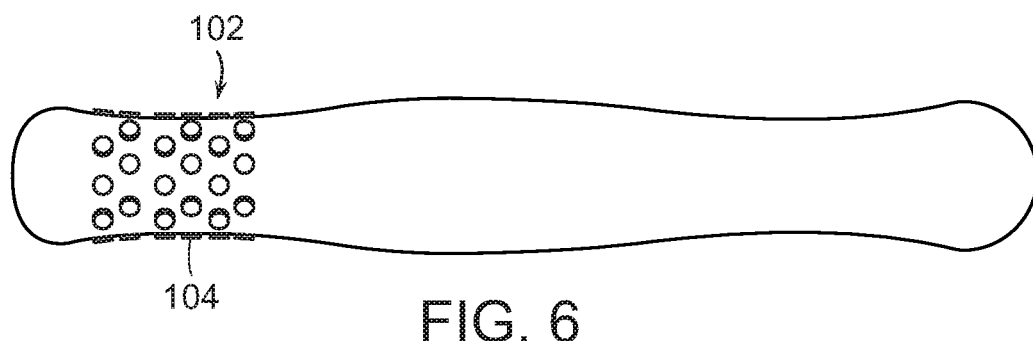
FIG. 6 is a view from the top or bottom of a contoured forceps sleeve having a textured region to enhance grasping by the thumb and forefinger of the user in accordance with a preferred embodiment of the present invention.
Figure 7:
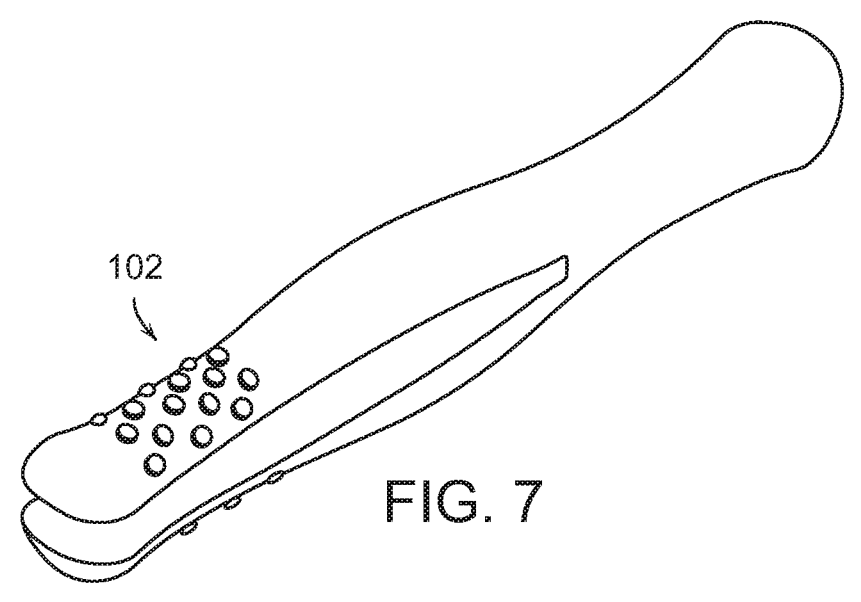
FIG. 7 is front side perspective view of a contoured forceps sleeve having a textured region to enhance grasping by the thumb and forefinger of the user in accordance with a preferred embodiment of the present invention.
Figure 8A:
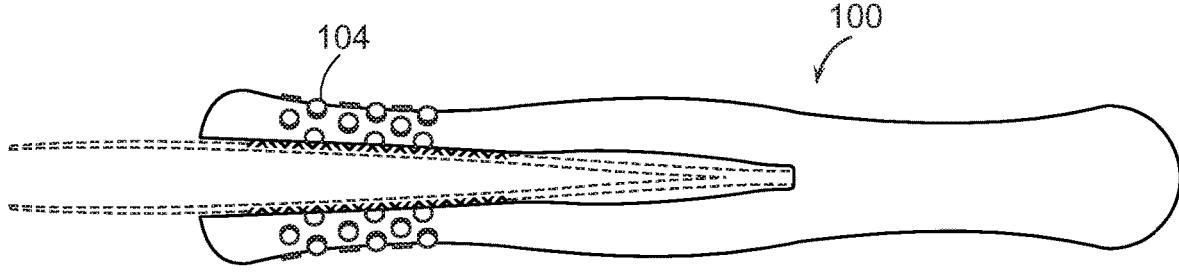
FIGS. 8A-8B are side views of a contoured forceps sleeve having a textured region to enhance grasping by the thumb and forefinger and forceps in the open and closed positions, respectively, in accordance with a preferred embodiment of the present invention.
Figure 8B:
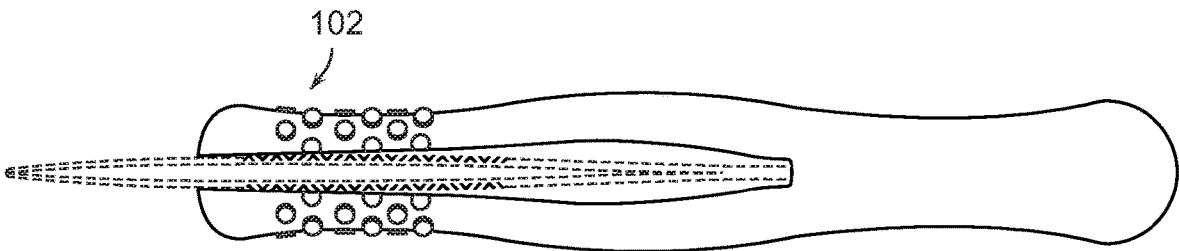

FIG. 4A illustrates a side view of the adaptor 10 combined with existing forceps 40. The forceps 40 are inserted into the cavity 16 such that the gripping surfaces 42 of the arms 44, 46 on the walls of the cavity 16 form the inner side or contact surfaces of the first arm 44 and the second arm 46. The proximal end of the forceps extends into an inner cavity 45, which extends into the proximal portion 12 of the adaptor sheath. The walls of the cavity 16 and the inner cavity 45 can be shaped to conform to the shape of the forceps 40 to securely grip the forceps during use. The inner surface of the cavity 16 and inner cavity 45 can also be scalloped or dimpled to engage the frictional surface features of the forceps. Alternatively, the arms 44 or 46 or the inner cavity 45 can be fitted with a "snap" feature that locks the forceps in place upon insertion.

The material and configuration of the arms 44 and 46 are adapted to be flexible to allow for the manipulation of the forceps blades. As shown in FIG. 4B, when force is applied to the first arm 44 and the second arm 46, the arms flex, moving relative to each other to translate the tips of the forceps towards each other to obtain a grasping position. When the force is withdrawn, the arms 44 and 46 move relatively away from each other to relax the blades of the forceps to an open position. The increased tactile feeling and area of contact between the user's fingers and the arms 44 and 46 allow the user to precisely control the force applied to the blades of the forceps. Such precise control force can be beneficial, especially when manipulating delicate structures, such as tissues, which cannot be gripped if too little force is applied, but which may be damaged if too much force is applied.

In one embodiment, the arms 44 and 46 are optimized to minimize the force required to compress the tips 47 of forceps 40 to further increase the control and tactile feedback of the system. Reducing compression resistance also has the benefit of minimizing hand fatigue from extended use. The structure in FIGS. 4A and 4B is a composite structure in which the mechanical properties of the metal component and the plastic component combine to define the resilient and torsional properties of the device.

Figure 12A:
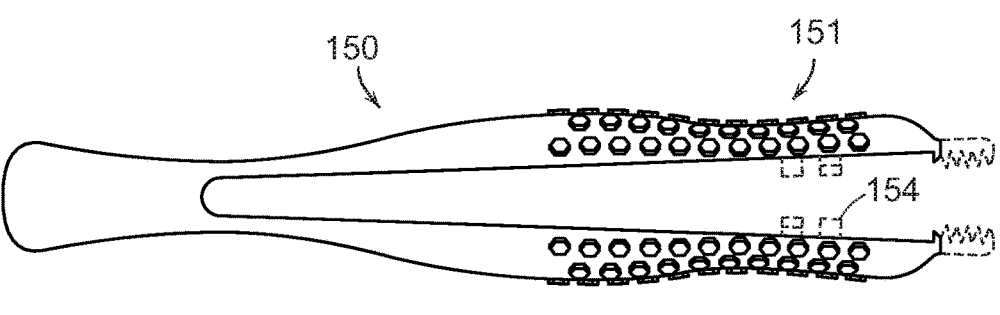
FIGS. 12A-12B are side views of a contoured forceps having a textured region to enhance grasping by the thumb and forefinger in open and closed positions, respectively, in accordance with a preferred embodiment of the present invention.
Figure 12B:
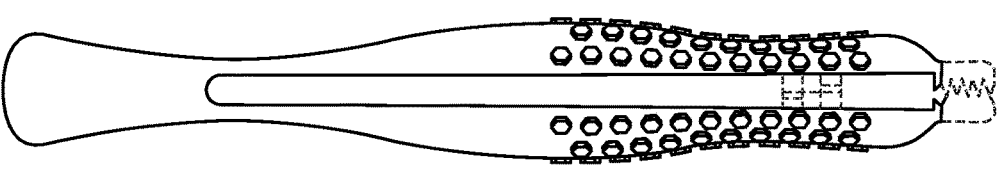
Figure 13:
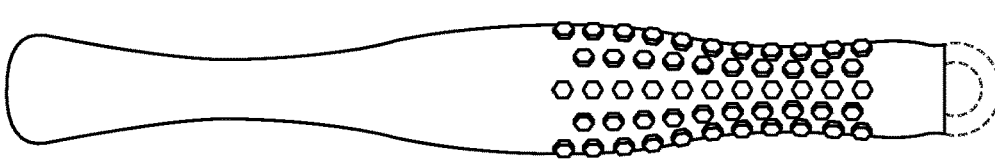
FIG. 13 is a view from the top or bottom of a contoured forceps having a textured region to enhance grasping by the thumb and forefinger in accordance with a preferred embodiment of the present invention.
Figure 14:
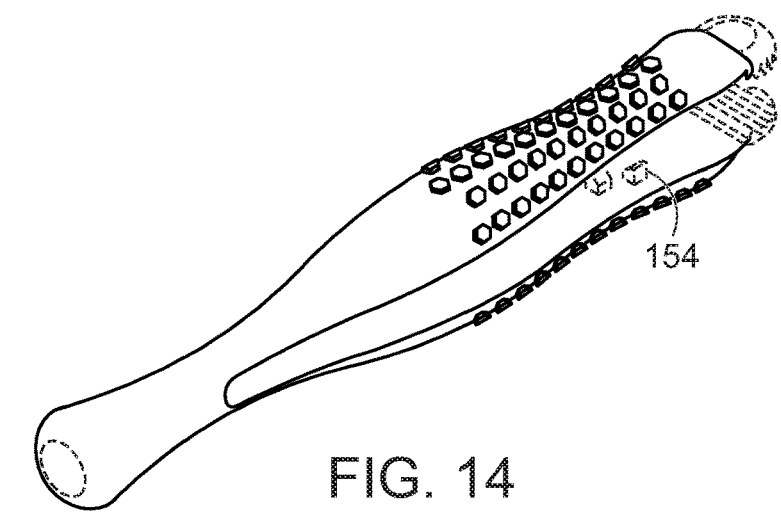
FIG. 14 is a rear side perspective view of a contoured forceps having a textured region to enhance grasping by the thumb and forefinger in accordance with a preferred embodiment of the present invention.
Figure 15:
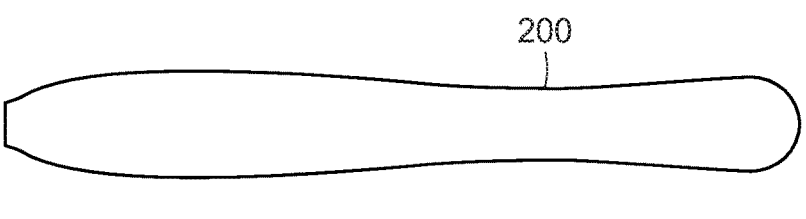
FIG. 15 is a top view of a contoured forceps onlay in accordance with a preferred embodiment of the present invention.
Figure 16:
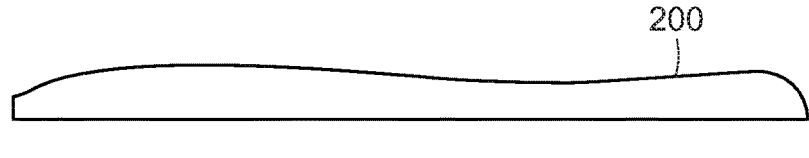
FIG. 16 is a side view of a contoured forceps onlay in accordance with a preferred embodiment of the present invention.
Figure 17A:
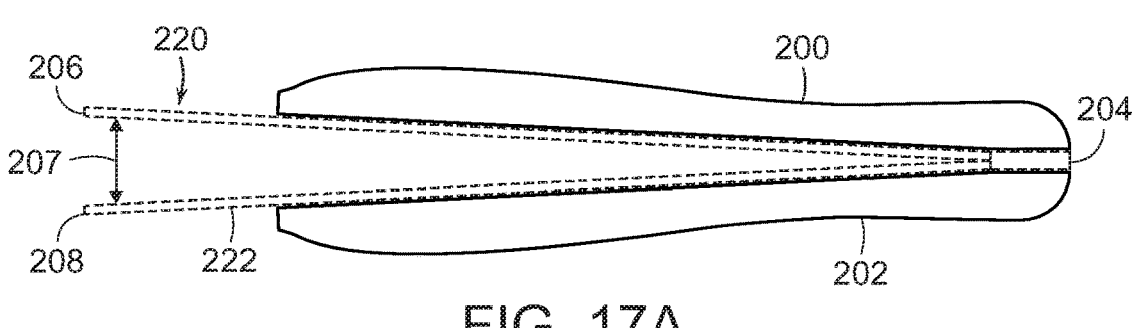
FIGS. 17A-17B are side views of contoured forceps onlays applied to forceps in open and closed positions, respectively, in accordance with a preferred embodiment of the present invention.
Figure 17B:
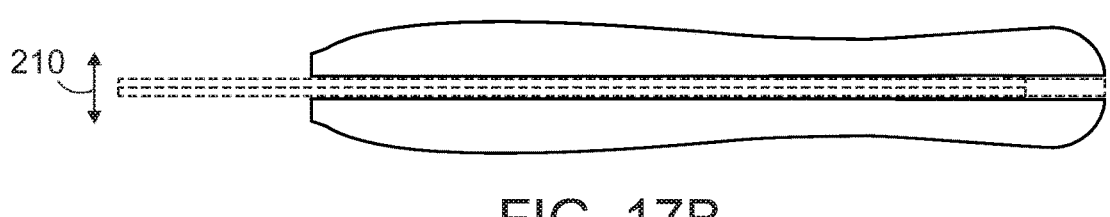
Figure 18:
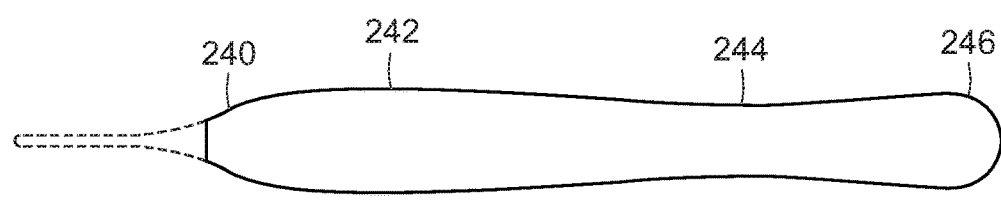
FIG. 18 is a top view of the forceps illustrated in FIGS. 17A-17B.
Figure 19:
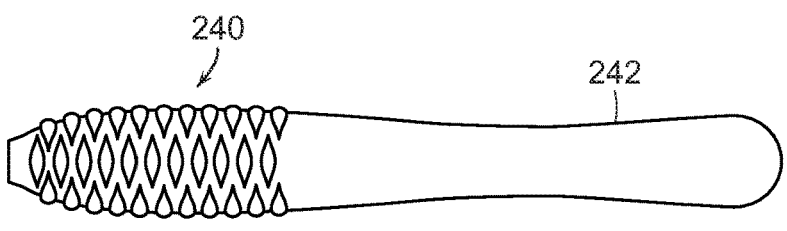
FIG. 19 is a top view of a contoured forceps onlay having a textured region to enhance grasping by the thumb and forefinger of the user in accordance with a preferred embodiment of the present invention.
Figure 20:
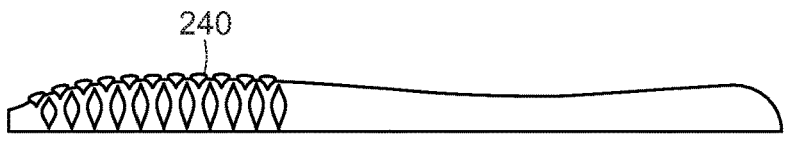
FIG. 20 is a side view of a contoured forceps onlay having a textured region to enhance grasping by the thumb and forefinger of the user in accordance with a preferred embodiment of the present invention.
Figure 21A:
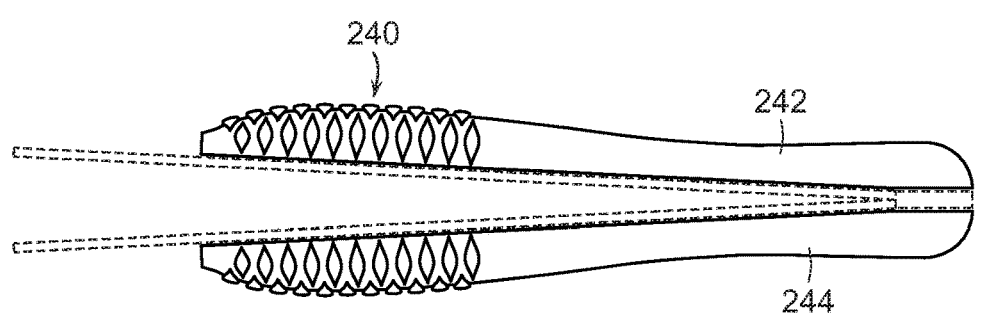
FIGS. 21A-21B are side views of contoured forceps onlays having a textured region to enhance grasping by the thumb and forefinger of the user applied to forceps in the open and closed positions, respectively, in accordance with a preferred embodiment of the present invention.
Figure 21B:
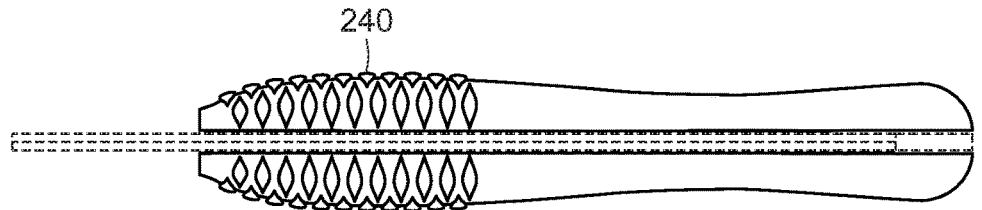
Figure 22:
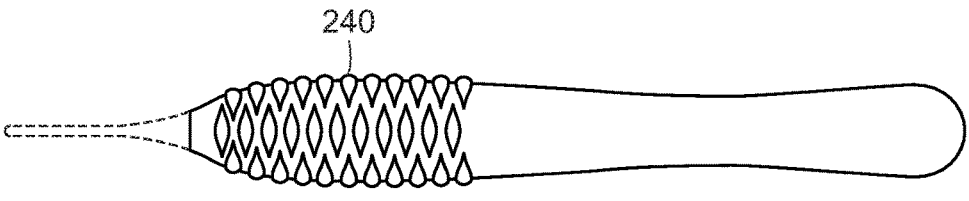
FIG. 22 is a view from the top or bottom of contoured forceps onlays having a textured region to enhance grasping by the thumb and forefinger of the user applied to forceps in accordance with a preferred embodiment of the present invention.

FIGS. 5 through 8 illustrate a further preferred embodiment of the adapter 100 where the user's grip and tactile feedback is further increased with the addition of a textured region 102 extending around the outer surfaces of both arms 444, 446 along the longitudinal axis of the adaptor. In various embodiments, the textured region 102 can comprise a plurality of raised nobs 104, hexagonal protrusions (FIG. 12), or diamond shaped protrusions (FIG. 19) among others. The textured region 102 can alternatively comprise a material, such as a gel, that forms to the contours of the user's hand and fingers. The textured region enhances the friction with the user's hand.

Figure 9A:
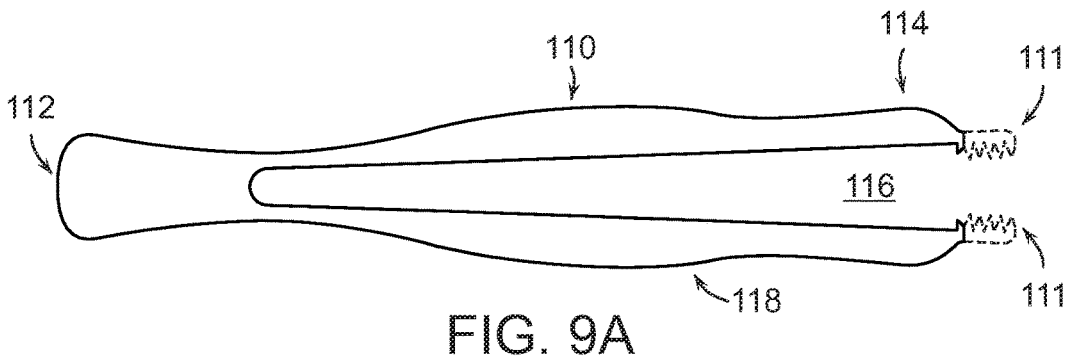
FIGS. 9A-9B are side views of a contoured forceps in the open and closed positions, respectively, in accordance with a preferred embodiment of the present invention.
Figure 9B:
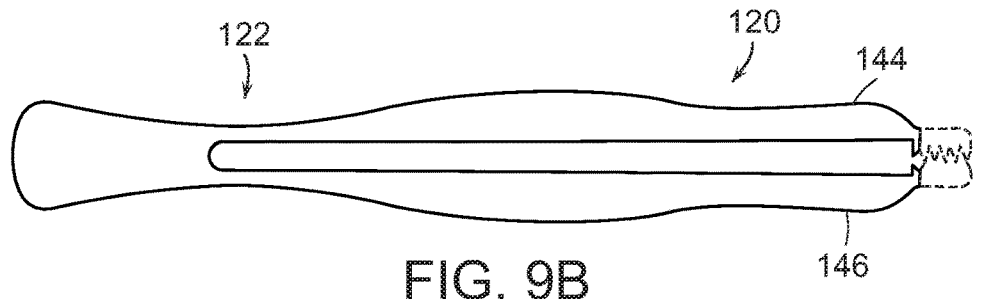
Figure 10:
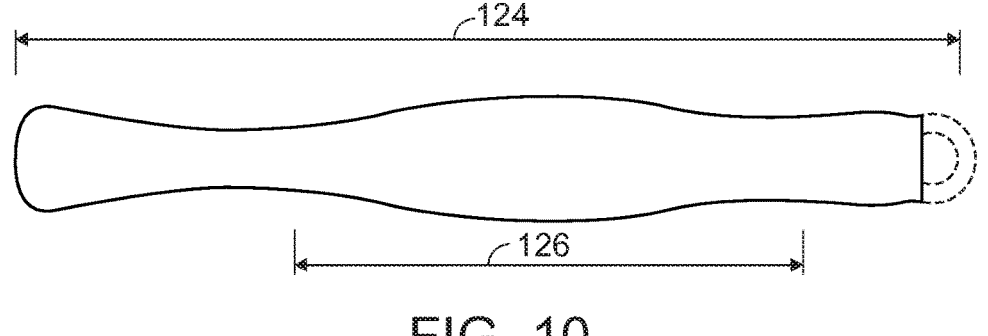
FIG. 10 is a view from the top or bottom of a contoured forceps in accordance with a preferred embodiment of the present invention.
Figure 11:
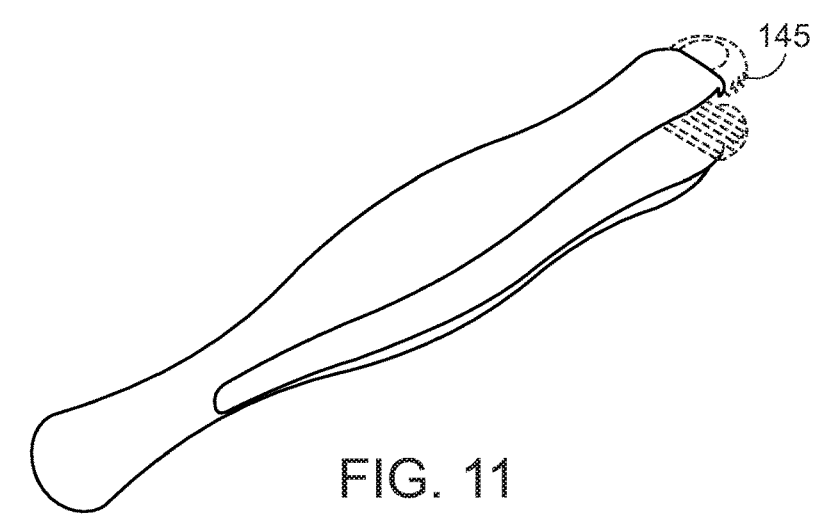
FIG. 11 is a rear side perspective view of a contoured forceps in accordance with a preferred embodiment of the present invention.

FIGS. 9A-11 illustrate a further preferred embodiment of the invention where a contoured forceps handle 110 includes integral forceps tips 111. FIG. 9A is a side view of the contoured forceps, which is divided into a proximal portion 112, a distal portion 114, and a central portion 118. The proximal portion 112 has a generally circular or elliptical cross-sectional shape. A cavity 116, which separates a first arm 144 from a second arm 146, extends through the distal portion 114, the central portion 118, and into the proximal portion 112.

Between the distal and central portions is a first concave section 120 or trough adapted to be grasped by the thumb/ forefinger and middle finger of the user. Between the central portion and the proximal portion is a second concave section 122 or trough adapted to rest in the web of the user's hand between the thumb and forefinger. The forceps can have a length 124 and a longitudinal distance 126 between the first and second troughs. The tips 111 can be flat, curved, have sharp edges or can have teeth 145.

FIGS. 12A through 14 illustrate a further preferred embodiment including a roughened surface region 151 to improve the frictional grasp of the forceps. The handles of the various embodiments of the present invention can include roughened surface region 151 to enhance the grasp of the user. The forceps is replaceable and can be sized for use with any of the embodiments of the invention described herein. The forceps 150 can include an elastic material that can be replaced when worn away or if a different shape, color, or texture is needed for a particular procedure. The elastic material can slide onto the arms. The inside walls of the cavity can include elements 154 that can attach the walls together.

Shown in FIGS. 15-18 is an embodiment in which contoured plastic forceps handle elements 200, 202 are attached to the arms of the forceps 220. This embodiment can utilize the contoured shapes used in other embodiments, or alternatively, can utilize the shape illustrated in FIGS. 15-16 having a proximal trough, a wider central region, and a smaller distal region. The elements can be bonded to the outer surfaces of the tongs or arms of a forceps. The user can then grasp and compress the arms from an open position (FIG. 17A) to a closed or grasping position (FIG. 17B). The spacing 207 between the arms 220 and 222 will be reduced when grasping an object, but are generally not abutting when in use. The grasping metal elements 220, 222 can also comprise separate plastic elements in another embodiment.

FIGS. 19-22 illustrate a further embodiment using a roughened surface region 240 for attachment to forceps. Unlike prior embodiments in the present application, the embodiments shown in FIGS. 15-22 provide a restoring force 210 upon release of pressure defined by the metal forcep elements 220, 222 that are bonded at the proximal ends 204. The distal ends have a separation. The plastic contoured elements 242, 244 are attached by adhesive or snap-on elements to the metal arms in this embodiment and do not substantially alter the spring characteristic thereof.

Figure 23A:
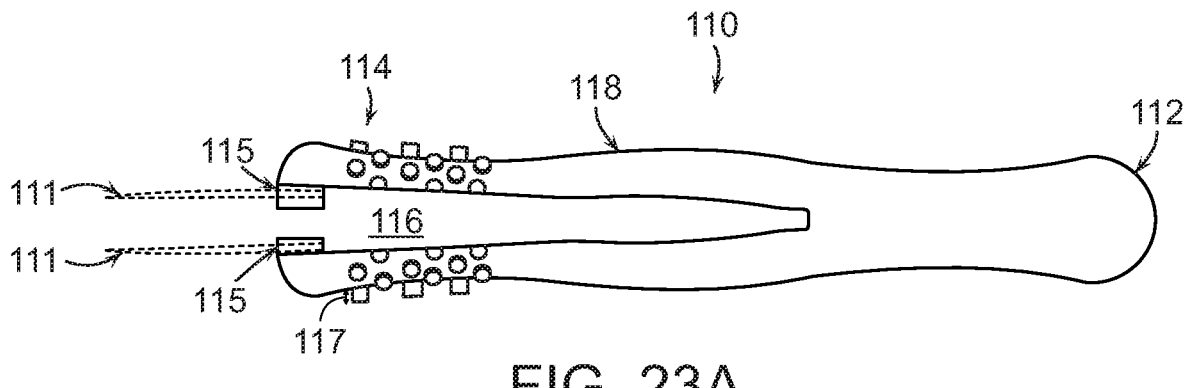
FIGS. 23A-23B are side views of a contoured forceps in open and closed positions, respectively, in accordance with a preferred embodiment of the present invention.
Figure 23B:
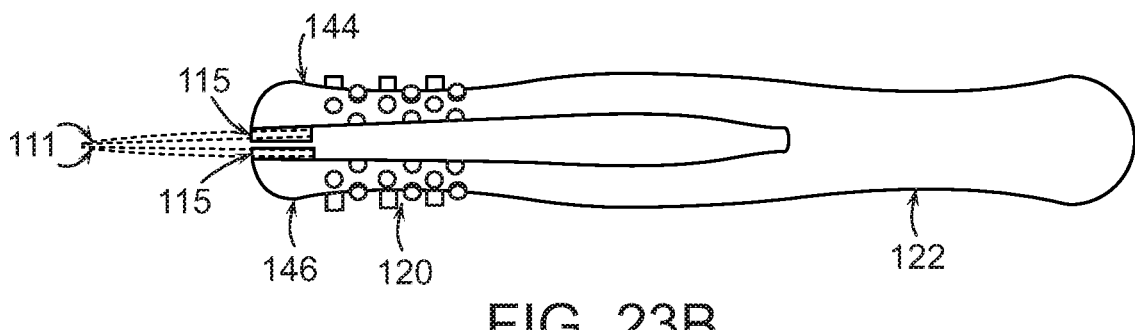

Shown in FIGS. 23A and 23B is an embodiment in which a contoured forceps handle 110 includes integral forceps tips 111. FIG. 23A is a side view of the contoured forceps, which is divided into a proximal portion 112, a distal portion 114, and a central portion 118. The proximal portion 112 has a generally circular or elliptical cross-sectional shape. A cavity 116, which separates a first arm 144 from a second arm 146, extends through the distal portion 114, the central portion 118, and into the proximal portion 112. In certain embodiments, the tips 111 may be integrated into the handle using an adhesive, a snap-fit, or by mounting with hardware such as a screw. The tips may be inset into the handle at ridges 115.

In accordance with certain embodiments, the textured region 102 can comprise larger diameter raised nubs or protrusions of greater thickness 117. As the user rotates the handle, the unbalanced force imparted by the user's hand to an edge of a nub causes that edge and the portion of the nub near the edge to compress. In this way, the nubs can provide feedback to the user's hand about the rotational attitude of the forceps as it is being held and moved by the user. This palpable feedback increases the user's ability to make fine-tuned adjustments to the rotation of the forceps while grasping and manipulating objects.

FIG. 24 illustrates a method 2400 for use of a surgical forceps. The method 2400 includes grasping 2402 a surgical forceps having a first contoured surface and a second contoured surface with a secondary hand. The method 2400 also includes compressing 2404 the arms of the surgical forceps to grasp an object. The method 2400 also includes rotating 2406 the surgical forceps while grasping the object during a surgical procedure.

The step of grasping 2402 a surgical forceps having a first contoured surface and a second contoured surface may be performed, for example but not limited to, grasping a surgical forceps having a roughened surface or a textured surface. In accordance with certain embodiments, the grasping 2402 step may be performed with a user's secondary hand (i.e., their non-preferred hand or "off" hand). In accordance with certain embodiments, the method 2400 may include an additional step of performing 2408 a surgical procedure using a tool in the primary (i.e. dominant) hand of the user while simultaneously manipulating tissue or objects with the surgical forceps.

FIG. 25 illustrates a method 2500 for assembling a surgical forceps. The method 2500 includes fabricating 2502 a forceps handle having a first arm and a second arm, the first arm having a first contoured surface and the second arm having a second contoured surface such that the forceps handle can be held in a hand of a user, each arm having a contoured surface that includes a distal trough, a larger central portion and a proximal trough extending along a longitudinal axis of each arm. The method 2500 also includes inserting 2504 a forceps between the first arm and the second arm.

The step of fabricating 2502 a forceps handle having a first arm and a second arm, the first arm having a first contoured surface and the second arm having a second contoured surface such that the forceps handle can be held in a hand of a user, each arm having a contoured surface that includes a distal trough, a larger central portion and a proximal trough extending along a longitudinal axis of each arm may be performed, for example but not limited to, using an injection molding process or a 3D printing process. In accordance with various embodiments, the first arm and the second arm of the fabricated handle may comprise textured or roughened surfaces at their proximal ends. These textured or roughened surfaces may comprise raised nobs, hexagonal protrusions, or diamond-shaped protrusions.

The claims should not be read as limited to the described order or elements unless stated to that effect. All embodiments that came within the scope and spirit of the following claims and equivalents thereto are claimed as the invention.

What is claimed is:

1. A surgical forceps comprising:

a forceps handle having a first metal arm attached to a second metal arm, the first metal arm having a first distal grasping surface and the second metal arm having a second distal grasping surface configured to grasp tissue;

wherein the first metal arm has a first contoured surface material and the second metal arm has a second contoured surface material, the forceps handle being configured to be held in a hand of a user such that the hand of the user can apply a compressive force in opposition to a spring force separating distal ends of the first metal arm and the second metal arm to reduce a distance between the first distal grasping surface and the second distal grasping surface, wherein the first contoured surface material and the second contoured surface material can be grasped by the hand of the user, the first contoured surface material and the second contoured surface material each having a rounded distal trough surface with elastic textured surface features positioned to prevent fingers of the user from sliding distally toward tips of the forceps, the rounded distal trough surface having a reduced lateral diameter that is positioned between a larger distal portion surface and a rounded larger central portion surface, wherein the rounded larger central portion surface extends to a rounded proximal trough surface, each surface being shaped at least partially around a longitudinal axis of each metal arm; and wherein the first contoured surface material comprises a first gripping surface positioned on the first metal arm that extends into the rounded distal trough surface and the second contoured surface material comprises a second gripping surface positioned on the second metal arm that extends into the rounded distal trough surface having the elastic textured surface features wherein the elastic textured features are configured to provide tactile feedback to the user such that the user can manually manipulate the forceps while grasping tissue without damaging the tissue.

2. The forceps of claim 1 wherein the first distal grasping surface includes a first tip on the first metal arm and wherein the second distal grasping surface includes a second tip on the second metal arm such that the tips undergo relative movement to grasp the tissue.

3. The forceps of claim 2 wherein the forceps handle and the first and second tips include plastic.

4. The forceps of claim 1 wherein the elastic textured surface features comprise raised protrusions that compress in response to manually applied pressure.

5. The forceps of claim 1 wherein a force required to move the arms between an open position and a grasping position is in a selected range.

6. The forceps of claim 1 wherein the elastic textured surface features have edges on the distal trough surface of each of the first contoured surface material and the second contoured surface material that compress upon manual rotation of the forceps.

7. The forceps of claim 6 wherein the elastic textured surface features comprise raised nobs, hexagonal protrusions, or diamond-shaped protrusions.

8. The forceps of claim 1 wherein a proximal portion of the forceps handle has a substantially circular or elliptical cross-section thereby providing the rounded proximal trough surface configured to provide manual rotation of the handle while the handle contacts a web of the hand of the user between a thumb and forefinger.

9. The forceps of claim 1 wherein the forceps handle is composed of a polymer material that is sterilizable.

10. The forceps of claim 1, wherein the first contoured surface material and the second contoured surface material provide friction that reduces slippage when operated by the hand of the user to grasp or contact the tissue to be moved in a surgical procedure.

11. The forceps of claim 1 wherein a cavity between the first metal arm and the second metal arm extends from a distal end of the forceps handle to the larger central portion surface.

12. The forceps of claim 11 wherein the cavity is defined by inside walls wherein each inside wall includes an element configured to attach the inside walls together.

13. The forceps of claim 1 wherein a distance between a minimum distal trough diameter and a minimum proximal trough diameter is in a range of 5 cm to 7 cm.

14. The forceps of claim 1 wherein the first metal arm and second metal arm comprise a unitary body.

15. The forceps of claim 14 wherein the unitary body comprises a molded body or a 3D printed body.

16. The forceps of claim 14 wherein the first metal arm and the second metal arm are connected at a proximal portion of the forceps to have a resilient property in response to the compressive force.

17. The forceps of claim 1, wherein the first metal arm, the second metal arm, the first contoured surface material, and the second contoured surface material form a composite forceps handle.

18. A surgical forceps comprising:
a forceps having a first metal arm and a second metal arm that are connected at a proximal portion of the forceps such that a user's hand can apply a compressive force to reduce a distance between distal ends of the first metal arm and the second metal arm in opposition to a spring force separating the distal ends of the first metal arm and the second metal arm;
a first forceps handle onlay having a first contoured top surface having a rounded shape about a first metal arm longitudinal axis;
a second forceps handle onlay having a second contoured top surface having a rounded shape about a second metal arm longitudinal axis; and
wherein the first metal arm, the second metal arm, the first contoured top surface and the second contoured top surface form a composite forceps handle that includes a rounded distal trough surface having a reduced lateral diameter on each contoured top surface that each have an elastic textured surface region positioned to prevent fingers of the user from sliding distally towards the distal ends, the elastic textured surface region positioned between a larger lateral diameter rounded distal portion and a larger lateral diameter rounded central portion and a rounded proximal trough surface extending along the top surface of each onlay and further wherein the first forceps handle onlay is attached to the first metal arm, the second forceps handle onlay is attached to the second metal arm, and the rounded proximal trough surface extends around the proximal portion of the forceps wherein the elastic textured surface region on each onlay is configured to provide tactile feedback to the user such that the user can manipulate the forceps while grasping tissue without damaging the tissue.

19. The forceps of claim 18 wherein the first and second forceps handle onlays are attached to the arms of the forceps with an adhesive.

20. The forceps of claim 18 wherein the elastic textured surface region extends to a position near the proximal ends of the first forceps handle onlay and the second forceps handle onlay.

21. The forceps of claim 20 wherein the elastic textured surface region comprises raised nobs, hexagonal protrusions, or diamond-shaped protrusions having compressing edges with a spacing configured for manual rotation by fingers of the user's hand.

22. The forceps of claim 18 wherein each onlay comprises the elastic textured surface region having protrusions.

23. A method of assembling a surgical forceps comprising:
fabricating a forceps handle having a first metal arm and a second metal arm connected at a proximal portion of the forceps handle and configured to compress together at respective distal ends to grasp tissue;
fabricating a first surface element and a second surface element; and
attaching the first surface element to the first metal arm and attaching the second surface element to the second metal arm such that the forceps handle includes an outer contoured surface configured to be held in a hand of a user such that the user can rotate the forceps while grasping an object with the forceps, the outer contoured surface including a rounded distal trough surface with a reduced lateral diameter on each surface element having an elastic textured surface region that compresses in response to manual pressure in opposition to a spring force separating the distal ends of the first metal arm and the second metal arm to indicate a tactile gripping pressure to the user, the elastic textured surface regions being positioned to prevent fingers of the user from sliding distally toward the distal ends of the metal arms, the elastic textured surface region positioned between a rounded larger lateral diameter distal portion surface and a rounded larger lateral diameter central portion surface extending along a longitudinal axis of each arm such that a distance between the distal ends of the first metal arm and the second metal arm can be manually compressed by the user's hand to sense grasping the tissue with the elastic textured surface regions at the tactile gripping pressure without damaging the tissue and wherein a rounded proximal trough surface extends along each surface element around the proximal portion of the forceps handle.

24. The method of claim 23 wherein fabricating the first surface element and the second surface element includes using an injection molding or 3D printing process to form a composite forceps handle.

25. The method of claim 23 wherein the elastic textured surface region comprises raised nobs, hexagonal protrusions, or diamond-shaped protrusions having a spacing configured for manual rotation by fingers of the user's hand.

26. The method of claim 23 wherein the elastic textured surface region comprises raised flexible elements on the outer contoured surface.

* * * * *